United States Patent
Nolan et al.

(10) Patent No.: US 6,921,736 B1
(45) Date of Patent: Jul. 26, 2005

(54) SIMPLY ASSEMBLED AND RECYCLABLE POLYMER-SUPPORTED OLEFIN METATHESIS CATALYSTS

(75) Inventors: Steven P. Nolan, New Orleans, LA (US); Laleh Jafarpour, Darlington (GB)

(73) Assignee: University of New Orleans Research and Technology Foundation, Inc., New Orleans, LA (US)

(*) Notice: Subject to any disclaimer, the term of this patent is extended or adjusted under 35 U.S.C. 154(b) by 515 days.

(21) Appl. No.: 09/907,526

(22) Filed: Jul. 17, 2001

Related U.S. Application Data
(60) Provisional application No. 60/218,717, filed on Jul. 17, 2000.

(51) Int. Cl.$^7$ .................................................. B01J 31/00
(52) U.S. Cl. ...................... 502/159; 502/155; 502/167; 502/152
(58) Field of Search ................................ 502/152, 155, 502/159, 167

(56) References Cited

U.S. PATENT DOCUMENTS

| | | | |
|---|---|---|---|
| 5,917,071 A * | 6/1999 | Grubbs et al. ................. 556/21 |
| 5,969,170 A * | 10/1999 | Grubbs et al. ................. 556/21 |
| 6,121,184 A * | 9/2000 | Druliner et al. ............. 502/159 |
| 6,271,315 B1 * | 8/2001 | Kiessling et al. ......... 525/326.1 |
| 6,291,616 B1 * | 9/2001 | Kiessling et al. ............ 526/171 |
| 6,426,419 B1 * | 7/2002 | Grubbs et al. ............... 548/101 |
| 6,521,799 B2 * | 2/2003 | Wagener et al. ............ 568/852 |
| 6,610,626 B2 * | 8/2003 | Grubbs et al. .............. 502/155 |
| 6,620,955 B1 * | 9/2003 | Pederson et al. ............. 556/21 |
| 2001/0039360 A1 * | 11/2001 | Grubbs et al. .............. 556/136 |
| 2002/0107138 A1 * | 8/2002 | Hoveyda et al. ............ 502/167 |
| 2003/0064884 A1 * | 4/2003 | Yao ............................ 502/159 |
| 2004/0087438 A1 * | 5/2004 | Blechert et al. ............ 502/159 |

FOREIGN PATENT DOCUMENTS
WO    WO 00/51339    * 3/2000

OTHER PUBLICATIONS
Huang et al., J. Am. Chem. Soc., vol. 121, No. 12, 1999, pp. 2674–2678.*
Schanz et al., Organometallics, vol. 18, No. 24, 1999, pp. 5187–5190.*
Jafarpour et al., Organometallics, vol. 19, No. 11, 2000, pp. 2055–2057.*
Scholl et al., Tetrahedron Letters, vol. 40, 1999, pp. 2247–2250.*

* cited by examiner

*Primary Examiner*—David Sample
*Assistant Examiner*—J. Pasterczyk
(74) *Attorney, Agent, or Firm*—Garvey, Smith, Nehrbass & Doody, L.L.C.; Seth M. Nehrbass

(57) ABSTRACT

A heterogeneous catalytic system for RCM is recyclable, shows reactivity, tolerates functional groups and performs with dienes and highly hindered substrates. This system can include one of the following on a macroporous polymer (such as a macroporous polydivinylbenzene):

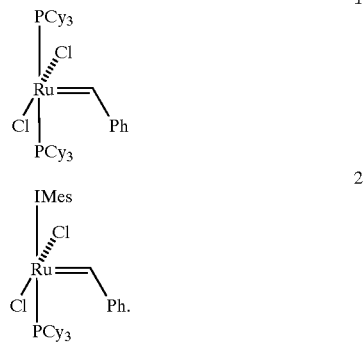

30 Claims, 2 Drawing Sheets

Fig. 1: Poly-DVB (Prior Art)

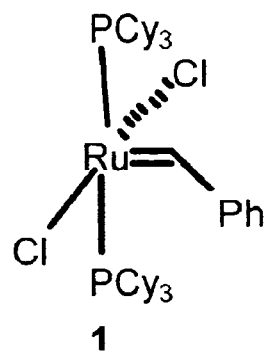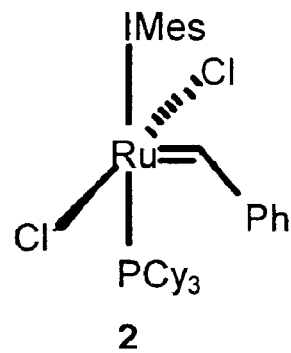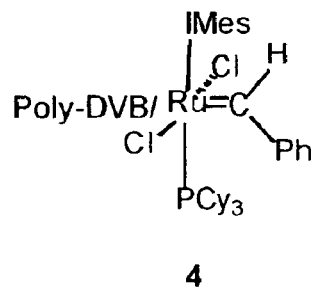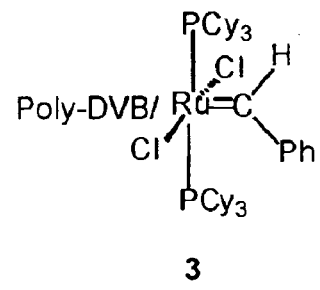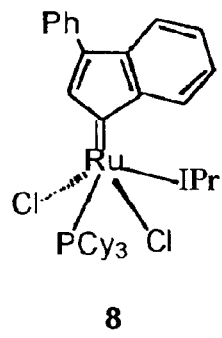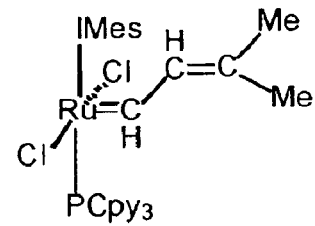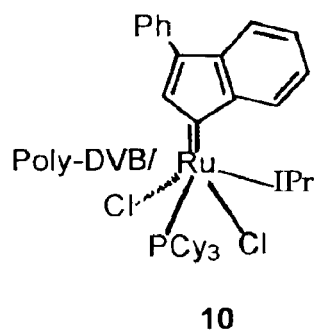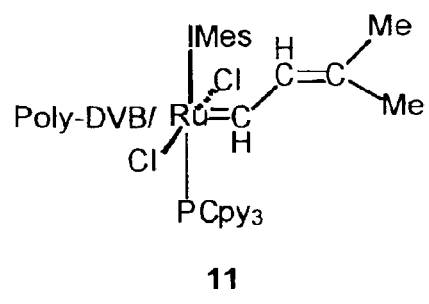
FIG. 2

SIMPLY ASSEMBLED AND RECYCLABLE POLYMER-SUPPORTED OLEFIN METATHESIS CATALYSTS

CROSS-REFERENCE TO RELATED APPLICATIONS

Priority of U.S. Provisional Patent Application Ser. No. 60/218,717, filed 17 Jul. 2000, incorporated herein by reference, is hereby claimed.

BACKGROUND OF THE INVENTION

1. Field of the Invention

The present invention relates to olefin metathesis. More particularly, the present invention relates to olefin metathesis catalysts.

2. General Background of the Invention

The formation of C—C bonds via olefin metathesis (e.g. Ring Closing Metathesis, RCM, or Ring Opening Metathesis Polymerization, ROMP) is a powerful technique in organic synthesis and polymer chemistry.[1] Well-defined, single-component metal-carbene complexes of the Grubbs type $(RuCl_2(=CHR)(PR'_3)_2$ (1) (see FIG. 2) are highly efficient catalyst precursor, moderately air and moisture sensitive and very tolerant of a variety of organic functional groups.[2] However, they exhibit low thermal stability and decompose at high temperatures.[3] It has been shown that the replacement of one of the phosphine ligand in the Grubbs system with a sterically demanding nucleophilic carbene ligand (e.g., N,N'-bis(mesityl)imidazol-2-ylidene, IMes) (2) (see FIG. 2) leads to increased thermal stability of the catalyst precursor and results in an increased RCM activity towards tri- and tetra-substituted dienes substrates.[3,4]

A common drawback of all above-mentioned catalyst precursors is their difficult recovery from reaction mixtures. These usually decompose upon work-up, giving rise to products that are highly colored by ruthenium residues.[5] These issues have been addressed by sequestering the ruthenium residues via addition of hydrophilic phosphine ligands[6] or lead compounds[7] in the work-up procedure, by phosphine derivatization leading to water-soluble olefin metathesis catalysts and applications in biphasic systems[8], and by the development of recyclable monomeric[9] (5) (see FIG. 2) and dendritic[10] ruthenium-based catalyst.

The simpler approach of anchoring an olefin metathesis catalyst to a polymer support should in theory lead to a straightforward recovery of the catalyst by filtration. Attempts have been made to heterogenize Grubbs catalyst by immobilizing it either through bis-phosphine linkages[11] or through the carbene moiety.[5] The former results in a two orders of magnitude decrease in catalytic activity compared to its homogeneous counterpart; and the latter, although displaying high activity in the initial cycle, exhibit significantly lower activity in subsequent cycles.[5]

The use of macroporous polymers as supports for transition metal catalysts has been explored.[12] Macroporous resins have a permanent well-developed porous structure even in a dry state.[13] Contrary to lightly cross-linked Merrifield resins[14], that need swelling solvents to access their interior volume, the pore structure of macroporous resins can be accessed by solvents and reactants without a need for swelling.[12]

The following U.S. Patents are incorporated herein by reference:
PAT. NO. Title
U.S. Pat. No. 6,049,017 Enhanced light olefin production
U.S. Pat. No. 6,030,917 Combinatorial synthesis and analysis of organometallic compounds and catalysts
U.S. Pat. No. 5,948,946 Use of sol-gel derived porous microposite of perfluorinated ion-exchange polymer and metal oxide to isomerize terminal olefins
U.S. Pat. No. 5,902,766 Alumoxanes, catalysts utilizing alumoxanes and polymers therefrom
U.S. Pat. No. 5,824,622 Porous microcomposite of perfluorinated ion-exchange polymer and metal oxide, a network of silica, or a network of metal oxide and silica derived via a sol-gel process
U.S. Pat. No. 5,639,900 Thermally activated olefin metathesis catalyst precursor
U.S. Pat. No. 5,606,085 Thermally activated olefin metathesis catalyst precursor
U.S. Pat. No. 5,569,635 Catalyst supports, supported catalysts and methods of making and using the same
U.S. Pat. No. 5,519,101 Process for preparation of unsaturated oligomers or polymers by acyclic olefin metathesis
U.S. Pat. No. 5,403,904 Process for preparation of telechelic difunctional unsaturated oligomers or polymers by acyclic olefin metathesis
U.S. Pat. No. 4,607,022 Olefin conversion catalyst
U.S. Pat. No. 4,547,617 Olefin conversion
U.S. Pat. No. 4,266,085 Olefin disproportionation process
U.S. Pat. No. 4,179,403 Resin-ligand-metal complex compositions

BRIEF SUMMARY OF THE INVENTION

The present invention comprises a simple heterogeneous catalytic system for RCM that is recyclable, shows comparable or better reactivity than its homogeneous counterparts, tolerates functional groups and performs very well with dienes and moderately well with highly hindered substrates.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein:

FIG. 2 shows catalyst precursors 1, 2, 8, and 9, and polymer supported analogs 3, 4, 10, and 11.

DETAILED DESCRIPTION OF THE INVENTION

Figure 1:
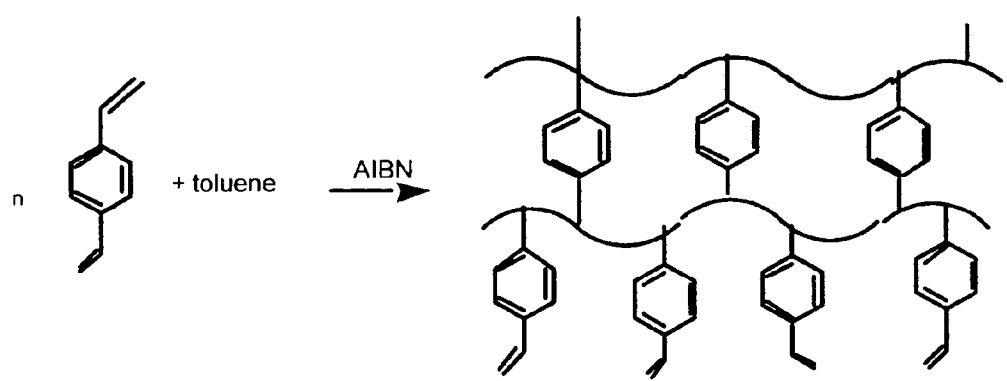
FIG. 1 shows poly-DVB.

Herein, we report the immobilization of olefin metathesis catalyst precursors 1 and 2 into a macroporous polymer. Their reactivity and recyclability in RCM reactions are also described.

The macroporous resin used (poly-divinylbenzene (poly-DVB)) was synthesized from divinylbenzene (DVB) with toluene as the porogen (v:v=1:1). Half of the bulk polymer was ground into a fine powder and the rest was crushed into small pieces and dried in vacuo. Poly-DVB has been characterized and found to have a relatively large surface area (810 mg/g polymer) where 55% of the vinyl groups are crosslinked, see FIG. 1.[15]

Ring closing metathesis catalyst precursors 1 and 2 were immobilized onto this support (power and small segment) by adding a toluene solution of the catalyst precursor to the polymer and heating to 50° C. The slurry was then filtered and washed with toluene to yield a light pink solid (1=>3 and 2=>4). The catalyst loading is estimated at 5 mol %/100 mg of polymer based on mass difference in empregnation experiments. Polymer-supported catalyst precursors 3 and 4 as small pieces and powder were used in RCM with a set of representative diene substrates.

TABLE 1

RCM of Diethyldiallylmalonate (5)

| Entry | Catalyst precursor | Form | Cycle | Time (hrs) | Yield[2] (%) |
|---|---|---|---|---|---|
| 1 | 1 | solution | — | 0.5 | 85[3] |
| 2 | 3 | powder | 1 | 0.5 | 97 |
| 3 | 3 | powder | 4 | 0.5 | 81 |
| 4 | 2 | solution | — | 0.5 | 92[3] |
| 5 | 4 | powder | 1 | 0.5 | 97 |
| 6 | 4 | powder | 4 | 0.5 | 81 |
| 7 | 4 | piece | 1 | 5.0 | 77 |
| 8 | 4 | piece | 6 | 5.0 | 55 |
| 9 | 4[4] | piece | 1 | 0.5 | 87 |
| 10 | 4[4] | piece | 2 | 0.5 | 17 |
| 11 | 4[5] | powder | 1 | 20.0 | 65 |

[1]All reactions are performed in $CH_2Cl_2$ and at room temperature.
[2]GC yield, average of two runs.
[3]NMR yield, average of two runs.
[4]One equivalent of CuCl was added to the reaction mixture.
[5]Reaction was carried out in methanol.

With the diene substrate diethyldiallylmalonate (5) (see FIG. 2) both 3 and 4 in powder

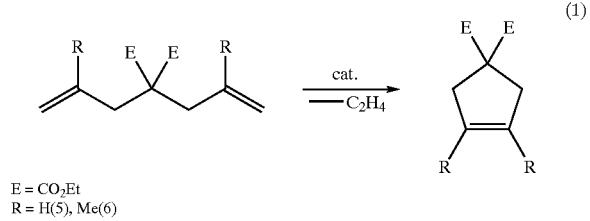

E = CO$_2$Et
R = H(5), Me(6)

form show RCM activity similar to the homogeneous catalysts (see Table 1). They can both be recycled up to 4 times without losing significant activity (Table 1 entries 2,3, 5,6). This combined with the fact that the filtrates and washes of six successive runs are $^{31}P$ NMR silent and the $^1H$ NMR displays no carbene resonance indicate that there is little or no leaching of the ruthenium complex in the solution phase.[16] The effect of the polymer surface area on catalysis was examined by comparing the RCM results of the catalyst precursor 4 in powder and small segment forms. When the powder of 4 was used in the RCM of 5, the reaction was complete in 30 minutes (Table 1, entry 2). The same reaction after 5 hours yielded only 77% product when the small solid piece of 4 was used (Table 1, entry 7). The solid segments can also be recycled efficiently up to six times (Table 1, entries 7,8). Addition of CuCl as a phosphine sponge (catalyst: CuCl=1:1), shown to increase catalytic activity[17], to 4 (as a solid segment) leads to a considerable initial rate increase but the resulting catalyst could not be recycled (Table 1, entries 9, 10). We believe that CuCl effectively removes the coordinated phosphine from the ruthenium complex and hence gives rise to a very reactive 14-electron ruthenium complex that decomposes leading to the marked decrease in the activity of the catalyst in the subsequent cycles. RCM of 5 with 4 also occurs in methanol albeit much slower than in CH$_2$Cl$_2$ (Table 1, entry 11). The homogeneous version of 4 displays no activity in methanol with this substrate.

The RCM of diallytosylamine (7) is very slow in the presence of catalyst precursor 2, however, the polymer-supported catalyst 4 ring closes 7 and can be recycled at least three times (Table 2, entries 2–3). The catalyst precursor 1 or its polymer-supported analogue 3 mediate this transformation very efficiently (Table 2, entries 6–7). Catalyst 3 can be recycled without significant loss of activity.

TABLE 2

RCM of diallytosylamine (7)

| Entry | Catalyst Precursor | Form | Cycle | Temp. (° C.) | Time (hrs) | Yield[2] (%) |
|---|---|---|---|---|---|---|
| 1 | 2 | solution | — | RT | 3.0 | 12[3] |
| 2 | 4 | powder | 1 | RT | 1.0 | 31 |
| 3 | 4 | powder | 3 | RT | 1.0 | 30 |
| 4 | 4 | piece | 1 | 40 | 3.0 | 71 |
| 5 | 4[4] | piece | 1 | 40 | 0.5 | 100 |
| 6 | 1 | solution | — | RT | 0.5 | 100[3] |
| 7 | 3 | powder | 1 | RT | 0.5 | 88 |

[1]All reactions were performed in $CH_2Cl_2$.
[2]GC yield, average of two runs.
[3]NMR yield, average of two runs.
[4]One equivalent of CuCl was added to the reaction mixture.

Highly substituted dienes have proven a challenge in RCM. To examine the performance of our supported catalysts, the tetra-substituted diene diethylbis(2-methylallyl)malonate 6 was examined as a RCM substrate. The catalyst precursor 1 and the polymer-supported relative 3 show no reactivity in the RCM of 6. However, 2 and the polymer-supported analogue 4 are active in this reaction. Moreover, 4 can be recycled up to four times without much loss of activity (33%, 38%, 28% and 22%). Addition of CuCl to either forms of 4 (power or pieces) does not increase the yield and results in a total loss of activity.

In conclusion, we have developed a simple heterogeneous catalyst system for RCM that is recyclable, shows comparable or better reactivity than its homogeneous counterparts, tolerates functional groups and performs very well with dienes and moderately well with highly hindered substrates. Studies aimed at exploring the extent of reactivity and mechanism of these and related supported catalysts are ongoing.

Acknowledgements L. J. acknowledges the NSERC of Canada for a postdoctoral fellowship. S. P. N. acknowledges the National Science Foundation, the Louisiana Board of Regents and the Petroleum Research Fund administered by the ACS for partial support of this work.

Supporting Information Available. Experimental procedures and data tables are given. This information is available free of charge via the internet at http://pubs.acs.org. It is also reproduced below:
Simply Assembled and Recyclable Polymer-Supported Olefin Metathesis Catalysts.
Laleh Jafarpour and Steven P. Nolan*
Department of Chemistry, University of New Orleans, New Orleans, La. 70148

SUPPORTING INFORMATION

Experimental
General Considerations: All reactions were carried out under an atmosphere of dry argon with standard Schlenk tube techniques or in a MBraun glovebox containing less than 1 ppm of oxygen and water. Anhydrous solvents were purchased from Aldrich and used as received. Divinylbenzene (tech. 55%) was purchased from Aldrich and degassed prior to use. Diethyldiallylmalonate was purchased from Aldrich, dried over P$_2$O$_5$, and vacuum distilled prior to use. Diallytosylamine[18], diethyldi(2-methylallyl)malonate[19] and PCy$_3$Ru(IMes)(=CHPh)Cl$_2$ (see text) were prepared according to literature procedures. The yields of the catalytic reactions were analyzed using a HP 5890 GC with a FID detector and HP-5 column. NMR spectra were recorded on a Oxford 400 MHz spectrometer. Elemental analyses were performed by Desert Analysis, Tuscon Ariz. Experimental synthetic procedures leading to the isolation of previously unreported complexes are described below.

Synthesis of Poly-DVB: In the glovebox, AIBN (1.5 wt. % of divinylbenzene, 0.066 g), divinylbenzene (tech., 55%, 4.44 g, 5 mL) and toluene (5 mL) were added to a 20 mL scintillation vial which was sealed with a teflon-coated screw-capped. The vial was then heated to 80° C. for 24 hours to give a white insoluble polymer. The vial was opened in the air, the polymer was scraped off the vial (to obtain small pieces) or ground to a powder. The solvent was removed in vacuo.

Synthesis of Polymer-Supported Ruthenium Catalysts 3 and 4: In the glovebox, poly-DVB (1.0 g) and the ruthenium catalyst 1 or 2 (10 wt. %, 0.1 g) and toluene (10 mL) were added to a Schlenk flask. The reaction mixtures was heated to 50° C. for 5 hours and stirred at room temperature for 12 hours. The slurry was then filtered on a Schlenk frit, washed with toluene (3×10 mL) and dried in vacuo to yield a pale pink solid.

General Procedure for Ring Closing Metathesis: In the glovebox, poly-DVB/Ru catalyst (100 mg), solvent (2 mL) and the substrate (1 M solution, 118 μL) were loaded in a Schlenk flask. The reaction mixture was heated under argon to temperatures shown in Tables 1–3. Product formation and diene disappearance were monitored by GC.

Experiments on the recycling and reuse of catalysts 3 and 4: After the allotted times mentioned in Tables 1–3 for each reaction, the polymer-supported catalyst precursors were filtered, washed with the same solvent used in the reactions and dried in vacuo. The catalysts were loaded into fresh Schlenk flasks and a fresh sample of the solvent (2 mL) was then added to each catalyst followed by another aliquot of the substrate (1M, 118 μL). The extent of reaction was then monitored by GC after the allotted time as mentioned in Tables 1–3.

TABLE 1

RCM of Diethyldiallylmalonate (5)[1]

| Entry | Catalyst | Form | Cycle | Time | Yield[2] (%) |
|---|---|---|---|---|---|
| 1 | 2 | solution | — | 0.5 | 92[3] |
| 2 | 4 | powder | 1 | 0.5 | 97 |
| 3 | 4 | powder | 2 | 0.5 | 97 |
| 4 | 4 | powder | 3 | 0.5 | 93 |
| 5 | 4 | powder | 4 | 0.5 | 81 |
| 6 | 4[4] | powder | 2 | 0.5 | 84 |
| 7 | 4 | pieces | 1 | 5.0 | 77 |
| 8 | 4 | pieces | 2 | 5.0 | 63 |
| 9 | 4 | pieces | 3 | 5.0 | 59 |
| 10 | 4 | pieces | 4 | 5.0 | 57 |
| 11 | 4 | pieces | 5 | 5.0 | 55 |
| 12 | 4 | pieces | 6 | 5.0 | 55 |
| 13 | 4[5] | pieces | 1 | 0.5 | 87 |
| 14 | 4[5] | pieces | 2 | 0.5 | 17 |
| 15 | 4[6] | powder | 1 | 20.0 | 65 |
| 16 | 1 | solution | — | 0.5 | 85[1] |
| 17 | 3 | powder | 1 | 0.5 | 97 |
| 18 | 3 | powder | 2 | 0.5 | 95 |
| 19 | 3 | powder | 3 | 0.5 | 93 |
| 20 | 3 | powder | 4 | 0.5 | 81 |
| 21 | 3[4] | powder | 2 | 0.5 | 86 |

[1]All reactions are performed in $CH_2Cl_2$ at room temperature.
[2]GC yield, average of two runs.
[3]NMR yield, average of two runs.
[4]Reaction was performed in air.
[5]One equivalent of CuCl was added to the reaction mixture.
[6]Reaction was carried out in methanol.

TABLE 2

RCM of diallytosylamine (7)[1]

| Entry | Catalyst Precursor | Form | Cycle | Temp. (° C.) | Time (hrs) | Yield[2] (%) |
|---|---|---|---|---|---|---|
| 1 | 2 | solution | — | RT | 3.0 | 12[1] |
| 2 | 4 | powder | 1 | RT | 1.0 | 31 |
| 3 | 4 | powder | 2 | RT | 1.0 | 38 |
| 4 | 4 | powder | 3 | RT | 1.0 | 30 |
| 5 | 4 | pieces | 1 | 40 | 3.0 | 71 |
| 6 | 4[4] | pieces | 1 | 40 | 0.5 | 100 |
| 7 | 1 | solution | — | RT | 0.5 | 100[3] |
| 8 | 3 | powder | 1 | RT | 0.5 | 88 |

[1]All reactions were performed in $CH_2Cl_2$.
[2]GC yield, average of two runs.
[3]NMR yield, average of two runs.
[4]One equivalent of CuCl was added to the reaction mixture.

TABLE 3

RCM of diethylbis(2-methylallyl)malonate (6)[1]

| Entry | Catalyst Precursor | Form | Cycle | Time (hrs) | Yield[2] (%) |
|---|---|---|---|---|---|
| 1 | 2 | solution | — | 1.0 | 75[3] |
| 2 | 4 | powder | 1 | 3.0 | 33 |
| 3 | 4 | powder | 2 | 3.0 | 36 |
| 4 | 4 | powder | 3 | 3.0 | 28 |
| 5 | 4 | powder | 4 | 3.0 | 22 |
| 6 | 4[4] | powder | 1 | 3.0 | 7 |
| 7 | 4[4] | pieces | 1 | 3.0 | 0 |
| 8 | 1 | solution | — | 3.0 | 0[3] |
| 9 | 3 | powder | 1 | 3.0 | 2 |

[1]All reactions were carried out in toluene and at 80° C.
[2]GC yield, average of two runs.
[3]NMR yield, average of two runs.
[4]One equivalent of CuCl was added to the reaction mixture.

Incorporated herein by reference are the papers attached to U.S. Provisional Patent Application Serial No. 60/218, 717 entitled "Simply Assembled and Recyclable Polymer-Supported Olefin Metathesis Catalysts" and "Simply Assembled and Recyclable Polymer-Supported Olefin Metathesis Catalysts—Supporting Information" and all references mentioned therein.

The homogeneous catalyst (8) (prior to being attached to the polymer to become analog (10)) can be found in Jafarpour, L. Scanz, H.-J.; Stevens, E. D.; Nolan, S. P., Organometallics, 1999, 18, 5416–5419.

The homogeneous catalyst (9) (prior to being attached to the polymer to become analog (11)) can be found in Huang, J.; Scanz, H.-J.; Stevens, E. D.; Nolan. S. P., Organometallics, 1999, 18, 5375–5382.

Catalyst precursors 1, 2, 8, and 9, and polymer supported analogs 3, 4, 10, and 11 referred to in the claims are shown in FIG. 2.

All measurements disclosed herein are at standard temperatures and pressures, at sea level on Earth, unless indicated otherwise. All materials used or intended to be used in a human being are biocompatible, unless indicated otherwise.

REFERENCES 1. (a) Grubbs, R. H.; Chang, S. Tetrahedron 1998, 54, 4413–4450 and the references therein. (b) Ivin, K. J. Mol. Catal. A: Chem, 1998, 133, 1–16. (c) Randall, M. L.; Snapper, M. L. J. Mol. Catal. A: Chem., 1998, 133, 29–40.

2. (a) Schwab, P.; France, M. B.; Ziller, J. W. Angew, Chem. Int. Ed. Engl. 1995, 34, 2039–2041, (b) Schwab, P.; Grubbs, R. H.; Ziller. J. W. J. Am. Chem. Soc. 1996,118, 100–110. (c) Diaz, E. L.; Nguyen, S. T.; Grubbs, R. H. *J. Am. Chem. Soc.* 1997,119,3887–3897 and references cited therein.

3. (a) Huang, J.; Stevens, E. D.; Nolan, S. P.; Petersen, J. L. *J. Am. Chem. Soc.* 1999, 121, 2674–2678. (b) Huang, J.; Schanz, H.-J.; Stevens, E. D.; Nolan, S. P. *Organometallics* 1999, 18, 5375–5380.

4. (a) Scholl, M.; Tinka, T. M.; Morgan, J. P.; Grubbs, R. H. *Tetrahedron Lett.* 1999, 40, 2247–2250. (b) Ackermann, L.; Fürstner, A.; Weskamp. T.; Kohl, F. J.; Herrmann, W. A. *Tetrahedron Lett.* 1999, 40, 4748–4790. (c) Schill, M.; Ding, S.; Lee, C. W.; Grubbs, R. H. *Org. Lett.* 1999, 1, 1751–1753. (d) Fürstner, A.; Thiel, O. R.; Ackermann, L.; Schanz, H.-J.; Nolan, S. P. *J. Org. Chem.* 2000, 65, 2204–2207. (e) Briot, A.; Bujard, M.; Gouverneur, V.; Nolan, S. P.; Nioskowski, C. *Org. Lett.* 2000, 2, 1517–1519.

5. Almed, M.; Barrett, A. G. M.; Braddock, D. C.; Cramp, S. M.; Procopiu, P. A. *Tetrahedron Lett.* 1999, 40, 8657–8662.

6. Maynard, H. D.; Grubbs, R. H. *Tetrahedron Lett.* 1999, 40, 4137–4140.

7. Paquette, L. A.; Schloss, J. D., Efremov, I.; Fabris, F.; Gallon, F.; Mendez-Andino, J.; Yang, J. *Org. Let.* 2000, 2,1259–1261.

8. Kirland, T. A.; Lynn, D. M.; Grubbs, R. H. *J. Org. Chem.* 1998, 63, 9904–9909.

9. Kingsbury, J. S.; Harrity, J. P. A.; Bonitatebus, P. J.; Hoveyda, A. H. *J. Am. Chem. Soc.* 1999, 121, 791–799.

10. Garber, S. B.; Kingsbury, S. J.; Gray, B. L.; Hoveyda, A. H. *J. Am. Chem. Soc.,* in press, personal communication.

11. Nguyen, S. T.; Grubbs, R. H. *J. Organomet. Chem.* 1995, 147, 195–200.

12. (a) Santora, B. P.; Larsen, A. O.; Gagné, M. R. *Organometallics* 1998, 18, 3138–3140, (b) Santora, B. P.; White, P. S.; Gagné, M. R. *Organometallics* 1999, 19, 2557–2560. (c) Taylor, R. A.; Santora, B. P.; Gagné, M. R. *Org. Let.* 2000, 2. In press (d) Canali, L.; Sherrington, D. C. *Chem. Soc. Rev.* 1999, 28, 85–93. (e) Nozaki, K.; Itoi, Y.; Sibahara, F.; Shirakawa, E.; Ohta, T.; Takaya, H.; Hiyama, T. *J. Am. Chem. Soc.* 1998, 120, 4051–4052. (f) Nozaki, K., Itoi, Y.; Sibahara, F.; Shirakawa, E.; Ohta, T.; Takaya, H.; Hiyama, T. *Bull Chem. Soc. Jpn.* 1999, 72, 1911–1918. (g) Polborn, K.; Severin, K. *Chem. Commun.* 1999, 2481–2482. (h) Salvadori, P.; Pini, D.; Petri, A. *J. Am. Chem. Soc.* 1997, 119, 6929–6930. (i)Matusi, J.; Nichollis, I. A.; Karube, I.; Mosbach, K. *J. Org. Chem.* 1996, 61, 5414–5417.

13. Sherrington, D. C. *Chem. Commun.* 1998, 2275–2286.

14. Pittman, C. U., Jr. *Polymer Supported Catalysts;* Wilkinson, G. Stone, F. G. A.; Able, E. W. Pergamon Press: Oxford, 1983: Vol. 8, pp 553–611.

15. (a) Santora, B. P.; Gagné, M. R.; Moloy, K. G.; Radu, N. S. *Macromolecules,* in press (b) Law, R. V.; Sherrington, D. C.; Snape, C. E. *Macromolecules* 1997, 30, 2868–2875.

16. Ongoing studies are aimed at quantifying the amount of leaching by AA and ICPMS.

17. For reference on use of CuCl as phosphine sponge see ref. 2c.

18. Fürstner, A.; Ackerman, L. *Chem. Commun.* 1999, 95–96.

19. Kirkland, T. A.; Grubbs, R. H. *J. Org. Chem.* 1997, 62, 1310–1318.

The foregoing embodiments are presented by way of example only; the scope of the present invention is to be limited only by the following claims.

What is claimed is:

1. A complex comprising:

olefin metathesis catalyst precursors 1 and/or 2 immobilized on a macroporous polymer, where 1 and 2 are defines as follows:

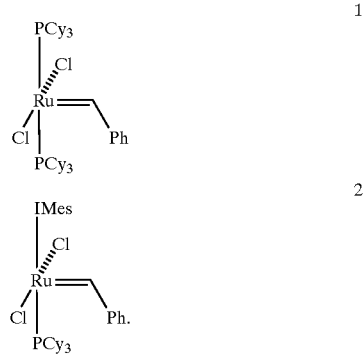

2. The complex of claim 1, wherein the macroporous polymer is poly-DVB.

3. The complex of claim 2, wherein the poly-DVB is synthesized from divinylbenzene with toluene as a porogen (v:v=1:1).

4. The complex of claim 2, wherein the poly-DVB is ground into a powder.

5. The complex of claim 1, wherein olefin metathesis catalyst precursors 1 and/or 2 are immobilized on the polymer by adding a toluene solution of the catalyst precursors to the polymer and heating to about 25–50° C.

6. The complex of claim 1, wherein the olefin metathesis catalyst precursors 1 and/or 2 are immobilized on the polymer by adding a toluene solution of the catalyst precursors to the polymer and heating to about 25–50° C. to produce a slurry, and the slurry is filtered and washed with toluene to yield a pink solid (1=>3 and 2=>4), where 3 and 4 are defined as follows:

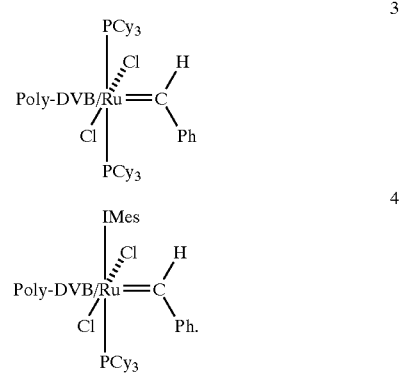

7. A complex comprising:

polymer supported analogs 3 and/or 4, where 3 and 4 are defined as follows:

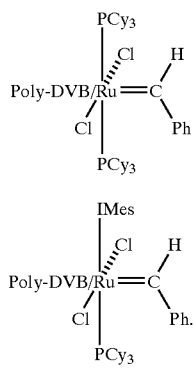

8. A heterogeneous catalytic system comprising:

polymer supported analogs 3 and/or 4, where 3 and 4 are defined as follows:

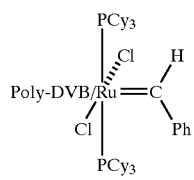

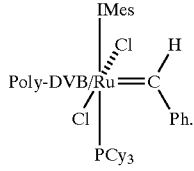

9. A method of making polymer supported analogs 3 and/or 4, comprising the following steps:

providing a macroporous polymer;
providing olefin metathesis catalyst precursors 1 and/or 2;
immobilizing olefin metathesis catalyst precursors 1 and/or 2 on the macroporous polymer, where 1, 2, 3, and 4 are defined as follows:

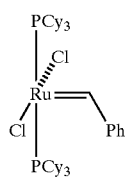

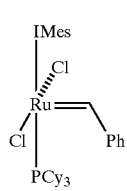

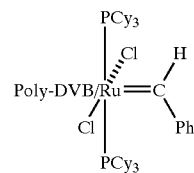

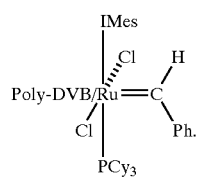

10. The complex of claim 1, wherein the macroporous polymer is a polymer containing a pendant olefin group.

11. The method of claim 9, wherein the poly-DVB is synthesized from divinylbenzene with toluene as a porogen (v:v=1:1).

12. The method of claim 9, wherein the poly-DVB is ground into a powder.

13. The method of claim 9, wherein olefin metathesis catalyst precursors 1 and/or 2 are immobilized onto the polymer by adding a toluene solution of the catalyst precursor to the polymer and heating to about 25–50° C.

14. The method of claim 9, wherein olefin metathesis catalyst precursors 1 and/or 2 are immobilized onto the polymer by adding a toluene solution of the catalyst precursor to the polymer and heating to about 25–50° C. to produce a slurry, and the slurry is filtered and washed with toluene to yield a pink solid (1=>2 and 2=>4).

15. A method of making polymer supported analogs 3 and/or 4 and/or 10 and/or 11, comprising the following steps:

providing a macroporous polymer;
providing at least one olefin metathesis catalyst precursor from the group consisting of olefin metathesis catalyst precursors 1, 2, 8, and 9;
immobilizing the olefin metathesis catalyst precursor(s) on the macroporous polymer, where 1, 2, 3, 4, 8, 9, 10, and 11 are defined as follows:

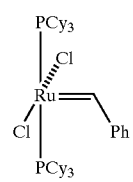

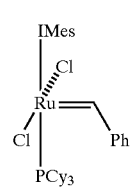

-continued

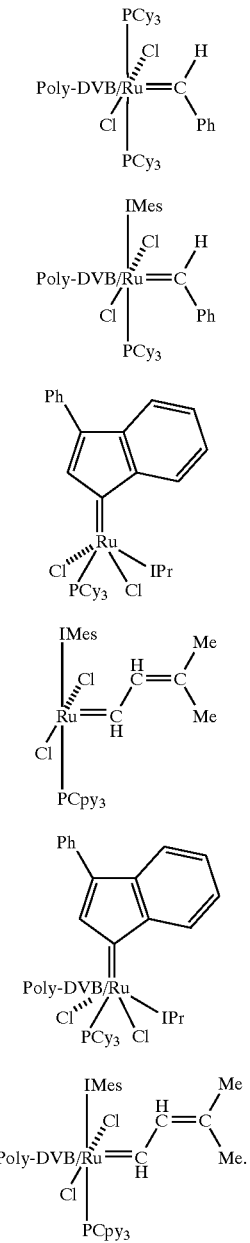

16. The method of claim 15, wherein the macroporous polymer is poly-DVB.

17. The method of claim 16, wherein the poly-DVB is synthesized from divinylbenzene with toluene as a porogen (v:v=1:1).

18. The method of claim 16, wherein the poly-DVB is ground into a powder.

19. The method of claim 15, wherein the olefin metathesis catalyst precursor(s) is immobilized onto the polymer by adding a toluene solution of the catalyst precursor to the polymer and heating to about 25–50° C.

20. The method of claim 19, wherein the olefin metathesis catalyst precursor(s) is immobilized onto the polymer by adding a toluene solution of the catalyst precursor to the polymer and heating to about 25–50° C. to produce a slurry, and the slurry is filtered and washed with toluene to yield a pink solid (1=>3, 2=>4, 8=>10, 9=>11).

21. A complex comprising:
at least one olefin metathesis catalyst precursor selected from the group consisting of olefin metathesis catalyst precursors 1, 2, 8, and 9, immobilized on a macroporous polymer, where 1, 2, 8, and 9 are defined as follows:

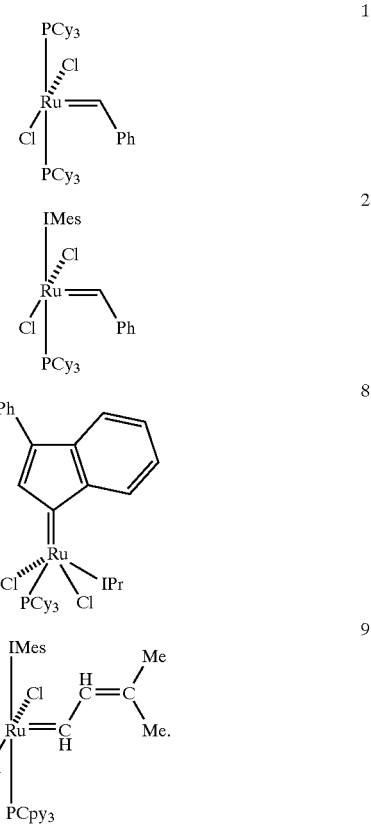

22. The complex of claim 21, wherein the macroporous polymer is poly-DVB.

23. The complex of claim 22, wherein the poly-DVB is synthesized from divinylbenzene with toluene as a porogen (v:v=1:1).

24. The complex of claim 22, wherein the poly-DVB is ground into a powder.

25. The complex of claim 21, wherein the olefin metathesis catalyst precursor is immobilized on the polymer by adding a toluene solution of the catalyst precursors to the polymer and heating to about 25–50° C.

26. The complex of claim 21, wherein the olefin metathesis catalyst precursor is immobilized on the polymer by adding a toluene solution of the catalyst precursors to the polymer and heating to about 25–50° C. to produce a slurry, and the slurry is filtered and washed with toluene to yield a pink solid (1=>3, 2=>4, 8=>10, 9=>11), where 3, 4, 10, and 11 are defined as follows:

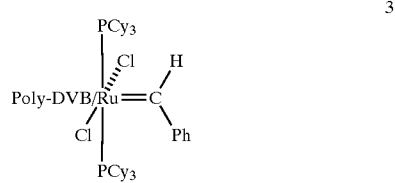

-continued

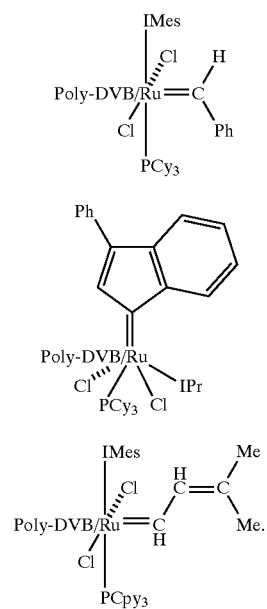

27. The complex of claim 21, wherein the macroporous polymer is a polymer containing a pendant olefin group.

28. A heterogeneous catalytic system comprising at least one polymer supported analog selected from the group consisting of polymer supported analogs 3, 4, 10, and 11, where 3, 4, 10, and 11 are defined as follows:

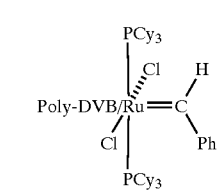

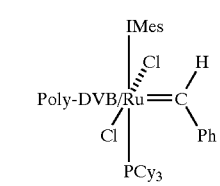

29. A polymer supported analog comprising at least one selected from the group consisting of:

polymer supported analogs 3, 4, 10, and 11, where 3, 4, 10, and 11 are defined as follows:

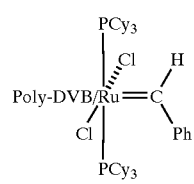

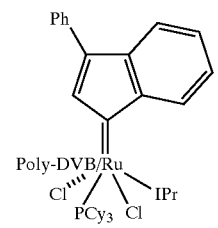

30. A polymer supported analog comprising:

polymer supported analogs 10 and/or 11, where 10 and 11 are defined as follows:

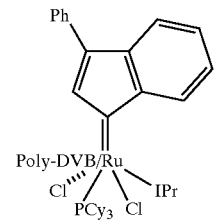

* * * * *